United States Patent [19]

Maerkl et al.

[11] Patent Number: 4,894,474
[45] Date of Patent: Jan. 16, 1990

[54] PREPARATION OF ALKYL PENTENOATES

[75] Inventors: Robert Maerkl, Fussgoenheim; Werner Bertleff, Viernheim; Hans J. Wilfinger, Schifferstadt; Gunter Schuch, Ludwigshafen; Wolfgang Harder, Weinheim; Gebhard Kuehn, Ludwigshafen; Paul Panitz, Worms, all of Fed. Rep. of Germany

[73] Assignee: BASF Aktiengesellschaft, Ludwigshafen, Fed. Rep. of Germany

[21] Appl. No.: 225,823

[22] Filed: Jul. 29, 1988

[30] Foreign Application Priority Data

Jul. 30, 1987 [DE] Fed. Rep. of Germany ....... 3725241

[51] Int. Cl.$^4$ .............................................. C07C 67/36
[52] U.S. Cl. ..................................... 560/206; 560/207
[58] Field of Search ......................................... 560/200

[56] References Cited

U.S. PATENT DOCUMENTS 4,303,589 12/1981 Chen ........................... 260/410.9 R
4,332,966 6/1982 Isogai et al. ........................ 560/206
4,350,668 9/1982 Isogai et al. ........................ 560/206
4,404,394 9/1983 Isogai et al. ........................ 560/200
4,550,195 10/1985 Platz et al. ........................ 560/206

FOREIGN PATENT DOCUMENTS 25112 3/1981 European Pat. Off. .
95431A 11/1983 European Pat. Off. .

OTHER PUBLICATIONS

Chem Soc. of Japan, Bd. 46 (1973), 526-27.
Patent Abstracts of Japan, vol. 6, No. 7(C-87), 1982
European Search Report.

Primary Examiner—Paul J. Killos
Attorney, Agent, or Firm—Keil & Weinkauf

[57] ABSTRACT

Alkyl pentenoates are prepared by reacting butadiene with carbon monoxide and an alkanol in the presence of a cobalt carbonyl complex and a tertiary, aromatic heterocyclic nitrogen base at from 80° to 160° C. under from 100 to 1,000 bar in the presence of from 0.1 to 10% by volume of hydrogen, based on the amount of carbon monoxide used.

20 Claims, No Drawings

PREPARATION OF ALKYL PENTENOATES

The present invention relates to a process for preparing alkyl pentenoates by reacting butadiene with carbon monoxide and alkanols in the presence of cobalt carbonyl complexes and tertiary nitrogen bases.

U.S. Pat. No. 4,550,195 discloses a process for preparing alkyl pentenoates by reacting a butadiene-containing $C_4$ cut with carbon monoxide and alkanols in the presence of cobalt carbonyl catalysts and heterocyclic aromatic tertiary nitrogen bases. In the industrial practice of the process it had been found that the space-time yield leaves something to be desired, in particular when the carbon monoxide, which is used in excess, is recycled for reuse.

From Bull. Chem. Soc. Jap. 46 (1973), 526–27, it is also already known that methyl pentenoate is obtainable by reacting butadiene with carbon monoxide having a hydrogen content of about 26% by volume and methanol in the presence of cobalt carbonyl and pyridine. However, the use of hydrogen is not given a favorable verdict, because appreciable amounts of byproducts are produced, the selectivity methyl pentenoate is reduced and the presence of hydrogen has no accelerating effect on the carbalkoxylation of butadiene.

It is an object of the present invention in the preparation of alkyl pentenoates by carbalkoxylation of butadiene to increase the selectivity to alkyl pentenoate and the space-time yield without raising the proportion of byproducts produced.

We have found that this object is achieved with a process for preparing an alkyl pentenoate by reacting butadiene with carbon monoxide and an alkanol in the presence of a cobalt carbonyl complex and a tertiary aromatic heterocyclic nitrogen base at from 80° to 160° C. under from 100 to 1,000 bar in the presence of from 0.1 to 10% by volume of hydrogen, based on the amount of carbon monoxide used.

The novel process has the advantage of giving high selectivity and a high space-time yield without producing increased amounts of byproducts.

The presence of hydrogen was not indicated insofar as according to Bull. Chem. Soc. Jap. 46 (1973), 526, no accelerating effect on the carbalkoxylation of butadiene but a higher level of byproducts was likely.

The starting compound used is butadiene. It is also possible to use butadiene-containing hydrocarbon mixtures, in particular butadiene-containing $C_4$ cuts. Such $C_4$ cuts contain on average for example from 40 to 60% by weight of butadiene, from 20 to 35% by weight of isobutene, from 10 to 25% by weight of butene-1, from 2 to 15% by weight of butene-2 and from 1 to 10% by weight of butane.

Suitable alkanols have advantageously from 1 to 6 carbon atoms, in particular from 1 to 4 carbon atoms. Specific examples are: methanol, ethanol, isopropanol, butanol and hexanol. Particular preference is given to methanol.

The alkanol is generally used in excess, advantageously in an amount from 1.1 to 10 moles, in particular from 1.1 to 5 moles, of alkanol per mole of butadiene.

The reaction is carried out at from 80° to 160° C., in particular at from 100° to 150° C. Furthermore, a pressure of from 100 to 1,000 bar, in particular from 120 to 700 bar, is employed during the reaction.

The carbon monoxide is advantageously used in excess, for example in from 1.3 to 10 times the stoichiometrically required amount. If the process is carried out continuously, the carbon monoxide is recycled uninterruptedly and replenished with fresh carbon monoxide.

The cobalt carbonyl catalyst used is either prepared in situ from a cobalt salt, for example from a salt of cobalt with a fatty acid, such as cobalt formate, cobalt acetate, cobalt propionate or cobalt butyrate, or, advantageously, used ready-made as cobalt carbonyl. More particularly, it is advantageous to introduce the cobalt carbonyl catalyst into the reaction mixture in the form of a solution in butadiene or a $C_4$ cut. Such a solution is obtained for example by reacting an aqueous solution of a fatty acid cobalt salt with a mixture of carbon monoxide and hydrogen in the presence of activated carbon at from 100° to 160° C. under from 100 to 400 bar. The resulting cobalt carbonyl is then extracted from the aqueous solution with the olefinically unsaturated compound.

The reaction is carried out in the presence of a heterocyclic, aromatic tertiary nitrogen base, advantageously of a $pK_a$ from 6 to 9. Suitable nitrogen bases are for example 3-methylpyridine ($pK_a$ 6.0), 4-methylpyridine ($pK_a$ 6.0), 2,3-dimethylpyridine ($pK_a$ 6.6), 2,4-dimethylpyridine ($pK_a$ 7.0) and 3,5-dimethylpyridine ($pK_a$ 6.2). Of particular industrial importance are 3-methylpyridine and 4-methylpyridine. It is also possible to use mixtures of the nitrogen bases mentioned. It is particularly advantageous to use from 2 to 25 moles of the aforementioned nitrogen base per mole of cobalt carbonyl catalyst.

Per mole of butadiene it is advantageous to use from 0.01 to 0.25 mole of cobalt catalyst, in particular from 0.04 to 0.2 mole of cobalt catalyst.

According to the invention, from 0.1 to 10% by volume, in particular from 0.3 to 8% by volume, of hydrogen, based on the amount of carbon monoxide used, is present. In general, carbon monoxide and hydrogen are fed into the reaction together. However, it is also possible to add carbon monoxide and hydrogen separately. Advantageously, the reaction is carried out continuously, for example in a plurality of stages connected in series, for example from 2 to 4 stages, in particular loop reactors. A particular embodiment here comprises adding the hydrogen, for example in the first and/or subsequent stages, for example the second stage.

The process of the invention is carried out for example by using two stainless steel high pressure vessels connected in series, for example two loop reactors connected in series, and uninterruptedly adding to the first stage butadiene-containing $C_4$ cut, alkanol, cobalt carbonyl catalyst, heterocyclic aromatic tertiary nitrogen base, carbon monoxide and hydrogen in the specified ratios and maintaining the reaction mixture at the specified temperature and under the specified pressure. In the second stage, reaction mixture is removed at the rate of addition of the starting materials, and carbon monoxide and excess hydrogen are separated off and, replenished with fresh carbon monoxide and hydrogen, returned back into the starting mixture. The remaining reaction mixture, after it has been let down and the cobalt catalyst separated off, is worked up, for example by treatment in an aqueous acid medium with a gas which contains molecular oxygen, removal of the cobalt salt solution and distillation of the organic phase.

The process of the invention chiefly produces 3-pentenoic ester with varying amounts of 4- and 2-pentenoic esters which are suitable for preparing adipic esters.

The process of the invention is illustrated by the Examples which follow. Parts by weight bear the same relation to parts by volume as that of the kilogram to the liter.

EXAMPLE 1

A 260 parts by volume capacity high pressure vessel is charged from below with 33 parts by weight of $C_4$ cut containing 41% (m/m) of 1,3-butadiene, 20 parts by weight of 3-methylpyridine, 11 parts by weight of methanol, 1 part by weight of cobalt in the form of cobalt carbonyl and 27 parts by weight of a gas mixture comprising 82% by volume of carbon monoxide, 1% by volume of carbon dioxide, 3% by volume of nitrogen and 2% by volume of hydrogen, and 11% by volume of butenes in the course of 60 minutes. The carbonylation takes place at 135° C. under 650 bar. The product taken off at the top of the high pressure vessel is let down, and the gas which separates off is recycled into the synthesis. The excess $C_4$ hydrocarbons are then distilled off. They still contain 1,500 ppm of unconverted butadiene. The conversion based on butadiene is 99.78%, and the selectivity to methyl pentenoate 22%. The proportion of byproducts is 7.1%. The space-time yield is 0.1 kg of methyl pentenoate per liter of reaction space per hour.

COMPARATIVE EXAMPLE

The procedure of Example 1 is followed. The reaction vessel is charged per hour with 26.4 parts by weight of $C_4$ cut containing 41% (m/m) of 1,3-butadiene, 22.4 parts by weight of 3-methylpyridine, 8.8 parts by weight of methanol, 0.8 parts by weight of cobalt in the form of cobalt carbonyl and 21.6 parts by weight of a gas mixture comprising 83% by volume of carbon monoxide, 1% by volume of carbon dioxide, 3% by volume of nitrogen, 0.07% by volume of hydrogen and 12% by volume of butenes. The reaction takes place as described in Example 1. The conversion based on butadiene is 99.8%, and the selectivity to methyl pentenoate 92%. The proportion of by-products is 7.1%. The space-time yield is 0.081 kg of methyl pentenoate per liter of reaction space per hour.

We claim:

1. A process for preparing an alkyl pentenoate, comprising: reacting butadiene with carbon monoxide and an alkanol in the presence of a cobalt carbonyl complex and a tertiary aromatic heterocyclic nitrogen base at from 80° to 160° C. under from 100 to 1,000 bar in the presence of from 0.1 to 10% by volume of hydrogen, based on the amount of carbon monoxide used.

2. The process of claim 1, wherein carbon monoxide is recycled.

3. The process of claim 1, wherein a temperature of from 100° to 150° C. is maintained.

4. The process of claim 1, wherein a pressure of from 120 to 700 bar is maintained.

5. The process of claim 1, wherein 3-methylpyridine or 4-methylpyridine or a mixture thereof is used.

6. The process of claim 1, wherein a butadiene-containing $C_4$ is used.

7. The process of claim 1, wherein the alkanol has from 1 to 6 carbon atoms.

8. The process of claim 7, wherein the alkanol has from 1 to 4 carbon atoms.

9. The process of claim 7, wherein the alkanol is selected from the group comprising: methanol, ethanol, isopropanol, butanol and hexanol.

10. The process of claim 1, wherein 1.1 to 10 moles of alkanol are used per mole of butadiene.

11. The process of claim 10, wherein 1.1 to 5 moles of alkanol are used per mole of butadiene.

12. The process of claim 1, wherein carbon monoxide is used in excess at from 1.3 to 10 times the stoichiometric amount.

13. The process of claim 1, wherein the cobalt carbonyl complex is introduced into the reaction mixture in the form of a solution in butadiene.

14. The process of claim 1, wherein 0.01 to 0.25 moles of cobalt carbonyl complex per mole of butadiene is used.

15. The process of claim 14, wherein 0.01 to 0.2 moles of cobalt carbonyl complex per mole of butadiene is used.

16. The process of claim 1, wherein 0.3 to 8% by volume of hydrogen based on the amount of carbon monoxide is used.

17. The process of claim 1, wherein the reaction is carried out continuously in a plurality of stages connected in series.

18. The process of claim 17, wherein the reaction is carried out in a series of loop reactors and hydrogen is added at each stage.

19. The process of claim 17, wherein the reaction is carried out in from 2 to 4 stages.

20. A process for preparing an alkyl pentenoate, comprising:
    (a) adding to a first stage butadiene-containing $C_4$ cut, an alkanol, a cobalt carbonyl catalyst, a heterocyclic tertiary nitrogen base, carbon monoxide and 0.1 to 10% by volume of hydrogen;
    (b) reacting the butadiene with the carbon monoxide and alkanol at from 80° to 160° C. under from 100 to 1,000 bar;
    (c) removing the reaction mixture at a second stage at the rate of addition of the starting materials;
    (d) separating off the carbon monoxide and excess hydrogen; and
    (e) returning replenished carbon monoxide and hydrogen to the starting mixture.

* * * * *